US00PP12608P2

(12) United States Plant Patent
Hammett

(10) Patent No.: US PP12,608 P2
(45) Date of Patent: May 7, 2002

(54) NEMESIA PLANT NAMED 'NEMPEACH'

(75) Inventor: Keith Hammett, Massey (NZ)

(73) Assignee: Seaview Nurseries, Manurewa (AU)

( * ) Notice: Subject to any disclaimer, the term of this patent is extended or adjusted under 35 U.S.C. 154(b) by 0 days.

(21) Appl. No.: 09/837,582

(22) Filed: Apr. 19, 2001

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Nemesia plant named 'Nempeach', characterized by its upright and compact plant habit; freely branching growth habit; small leaves; and unique pinkish lavender-colored flowers.

1 Drawing Sheet

BACKGROUND OF THE INVENTION

The present invention relates to a new and distinct cultivar of Nemesia plant, botanically known as *Nemesia caerula* and referred to by the cultivar name Nempeach.

The new Nemesia is a product of a planned breeding program conducted by the Inventor in Auckland, New Zealand. The objective of the program is to create new compact Nemesia cultivars with bushy growth habit and unique flower colors.

The new Nemesia originated from a cross by the Inventor of a proprietary *Nemesia caerula* selection identified as code number 433/02 as the female, or seed, parent with a proprietary *Nemesia caerula* selection identified as code number 585/01 as the male, or pollen, parent. The cultivar Nempeach was discovered and selected by the Inventor as a flowering plant within the progeny of the stated cross in a controlled environment in Auckland, New Zealand in June, 1998.

Asexual reproduction of the new Nemesia by terminal cuttings taken in a controlled environment in Auckland, New Zealand since July, 1998, has shown that the unique features of this new Nemesia are stable and are reproduced true to type in successive generations.

SUMMARY OF THE INVENTION

The new Nemesia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Nempeach' and distinguish 'Nempeach' as a new and distinct cultivar:

1. Upright and compact plant habit.
2. Freely branching, bushy growth habit.
3. Small leaf size.
4. Unique pinkish lavender-colored flowers.

Plants of the new Nemesia differ primarily from plants of the parents, the proprietary selections of *Nemesia caerula*, and other known cultivars of *Nemesia caerula* in flower color.

BRIEF DESCRIPTION OF THE PHOTOGRAPHS

The accompanying colored photographs illustrate the overall appearance of the new Nemesia, showing the colors as true as it is reasonably possible to obtain in colored reproductions of this type. Colors in the photographs may differ slightly from the color values cited in the detailed botanical description which accurately describe the colors of the new Nemesia.

The photograph at the top of the sheet comprises a side perspective view of a typical potted plant of 'Nempeach' that was about 14 weeks old.

The photograph at the bottom of the sheet comprises a close-up view of typical flowers of 'Nempeach'.

DETAILED BOTANICAL DESCRIPTION

The following observations, measurements, values, and comparisons describe plants grown in Encinitas, Calif., in a polyethylene-covered greenhouse during the spring with day temperatures about 18° C. and night temperatures about 13° C. Plants were grown for 14 weeks in 20-cm containers with three plants per container and were pinched twice. Color references are made to The Royal Horticultural Society Colour Chart except where general terms of ordinary dictionary significance are used.

Botanical classification: *Nemesia caerula* cultivar Nempeach.

Parentage:

*Female parent.*—Proprietary *Nemesia caerula* selection identified as code number 433/02.

*Male parent.*—Proprietary *Nemesia caerula* selection identified as code number 585/01.

Propagation:

*Type.*—By cuttings.

*Time to initiate roots.*—Summer: About 10 days at 20° C. Winter: About 12 days at 15° C.

*Time to develop roots.*—Summer: About 26 days at 20° C. Winter: About 28 days at 15° C.

*Root description.*—Fine, fibrous.

Plant description:

*General appearance.*—Upright and compact plant habit; freely branching, bushy; typically about 15 to 20 laterals with numerous secondary laterals developing after pinching. Unique pinkish lavender-colored zygomorphic flowers. Moderately vigorous.

*Plant height.*—About 29.5 cm.

*Plant diameter or spread.*—About 14 cm.

*Lateral branches.*—Appearance: Slender and filamentous; square in cross-section. Length: About 26 cm. Diameter: About 1 mm. Internode length: About 3.7 cm. Texture: Glabrous. Color: 144A.

*Foliage description.*—Arrangement: Opposite, single. Quantity: About 7 per lateral branch. Shape: Lanceolate. Apex: Narrowly acute. Base: Acute. Length, lower leaves: About 2.8 cm. Width, lower leaves: About 7 mm. Margin: Very slightly serrate. Texture: Smooth. Venation pattern: Pinnate. Petiole length: About 2 mm. Petiole diameter: About 1 mm. Color: Young leaves, upper surface: 144A, slightly glossy. Young leaves, lower surface: 144B. Fully expanded leaves, upper surface: 146A, slightly glossy; venation, 146A. Fully expanded leaves, lower surface: 146B, venation, 146B. Petiole: 144A.

Flowering description:

*Flowers.*—Zygomorphic solitary flowers arranged on terminal racemes; flowering acropetally towards apex. Flowers two-lipped with nectar spur. Flowers open rapidly and continue to develop rapidly lasting for only one or two days. Petals drop, however ovary and calyx persistent. Not fragrant.

*Natural flowering season.*—Natural flowering season is spring to fall; flowering continuous during this period.

*Quantity of flowers.*—Freely flowering with about 15 flowers per raceme.

*Flower length.*—About 1.4 cm.

*Flower width.*—About 1 cm.

*Flower depth.*—About 6 mm, does not including nectar spur.

*Nectar spur length.*—About 3 mm.

*Flower aspect.*—Mostly outward.

*Flower buds.*—Shape: Flattened ovoid with spur. Length: About 7 mm. Diameter: About 4.5 mm. Color: 69D.

*Petals.*—Arrangement/shape: Four upper petals are fused at base to form an upright lobed banner lip; lower petal modified into a larger lip with nectar spur and convex oval protuberance which serves as pollinator nectar guide and landing platform. Apex: Rounded. Margin: Entire. Length: Upper lip petals: About 1 cm. Lower lip petal: About 7 mm. Width: Upper lip petals: About 1.5 cm. Lower lip petal: About 1 cm. Texture: Smooth, velvety. Color: When opening, upper surface: 75D. When opening, lower surface: 69D. Mature, upper surface: Upper petals: 54B to 54C; flower color shifting to 84B with overtones of 54D with subsequent development. Lower petal: Towards apex, 54B to 54C; towards base, 76A; oval protuberance, 7A; flower color shifting to 84B with overtones of 54D with subsequent development. Mature, lower surface: 56A. Spur: Close to 56A. Throat: 155D.

*Sepals.*—Quantity: Five-parted, star-shaped calyx. Shape: Elliptic. Apex: Acute. Margin: Entire. Calyx length: About 3 mm. Calyx diameter: About 4 mm. Texture: Pubescent. Color: Upper surface: 144B. Lower surface: 144A.

*Pedicel.*—Length: About 1.3 cm. Diameter: Less than 1 mm. Strength: Slender, but hold flowers outward. Angle: About 45° from the stem. Color: 144A.

*Androecium.*—Stamen number: Four per flower. Anther shape: Ovate. Anther size: Less than 5 mm. Anther color: 4A. Amount of pollen: Scarce. Pollen color: 4A.

*Gynoecium.*—Pistil number: One per flower. Stigma shape: Flattened. Pistil length: About 2 mm. Style length: Less than 1 mm. Style color: 144C. Stigma color: 144C. Ovary color: 144C.

*Seed.*—Seed production has not been observed on plants of the new Nemesia.

Disease/pest resistance: Plants of the new Nemesia have not been observed to be resistant to pathogens or pests common to Nemesia.

It is claimed:

1. A new and distinct cultivar of Nemesia plant named 'Nempeach', as illustrated and described.

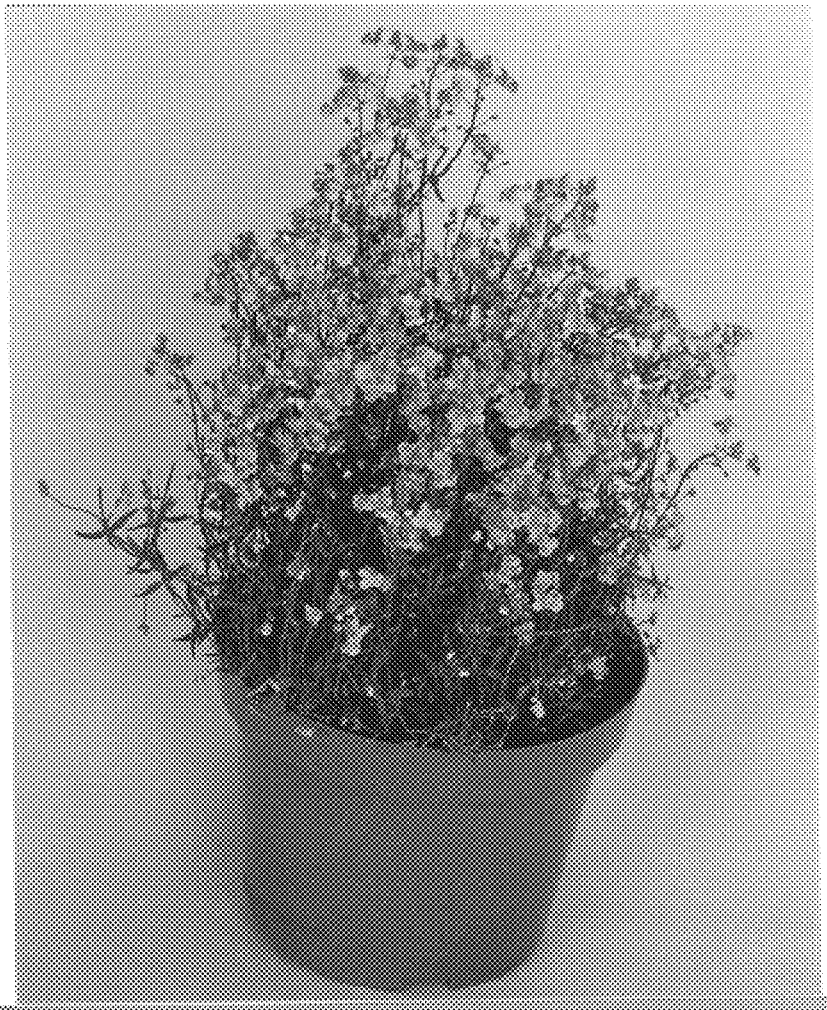
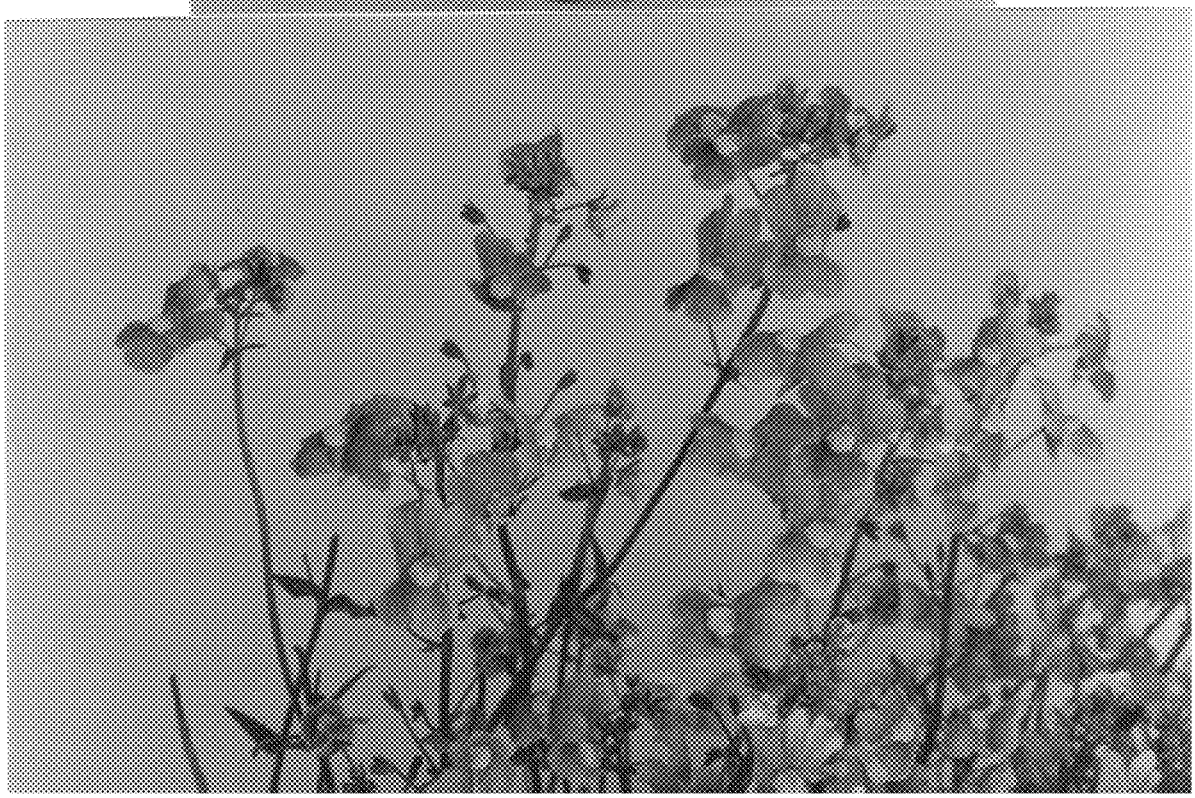

* * * * *